Figure 1:
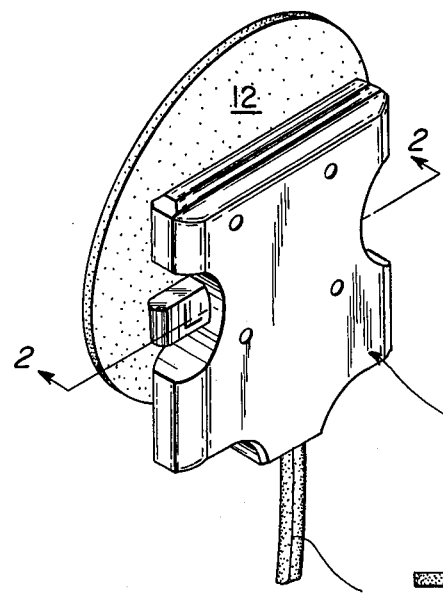

United States Patent [19]

Williams et al.

[11] 4,165,141

[45] Aug. 21, 1979

[54] LOCKING ELECTRICAL CONNECTOR

[75] Inventors: Frank R. Williams, Utica; William Abraham, New Hartford, both of N.Y.

[73] Assignee: Consolidated Medical Equipment Inc., Utica, N.Y.

[21] Appl. No.: 861,282

[22] Filed: Dec. 16, 1977

[51] Int. Cl.$^2$ .................... H01R 7/06; H01R 13/54
[52] U.S. Cl. .................. 339/75 R; 128/639; 339/254 R; 339/273 R
[58] Field of Search ............ 339/75 R, 238, 240, 339/247, 254 R, 254 M, 270 R, 273 R, 273 F, 273 S; 128/618

[56] References Cited
FOREIGN PATENT DOCUMENTS
115898 11/1917 United Kingdom ............... 339/254 R Primary Examiner—Roy Lake
Assistant Examiner—E. F. Desmond
Attorney, Agent, or Firm—Larson, Taylor and Hinds

[57] ABSTRACT

An electrical connector is provided for an electrode having a headed stud thereon in which a slot is provided between electrical contact plates mounted on the connector. The headed stud of the electrode fits within this slot and a slidable locking bar having a cam surface thereon is moved to a locking position wherein the headed stud is forced into a narrowed portion of the slot and is locked in contact with the electrical contact means.

4 Claims, 5 Drawing Figures

U.S. Patent    Aug. 21, 1979    4,165,141

LOCKING ELECTRICAL CONNECTOR

BACKGROUND OF THE INVENTION

I. Field of the Invention

The invention relates generally to the field of electrical connectors and more particularly, relates to connectors which are adapted to lock into contact with electrodes, specifically which are useful for contace with the body for electro-cardiograms, electro-surgery and the like.

II. Description of the Prior Art

Heretofore it has been a common practice to utilize body electrodes for the purpose of taking electroencephalogram readings or electro-cardiogram readings. Additionally body electrodes are used in electro-surgery as grounding pads to provide a return path for the current flow. There are a large number of prior art patents which are directed to body electrodes suitable for these purposes. For example, prior U.S. Pat. No. 3,841,312 issued Oct. 15, 1974 discloses an electrode which is particularly well suited for an electroencephalogram or electro-cardiogram reading. Pending application Ser. No. 684,317 filed May 7, 1976 discloses an electrode which is particularly well suited for use as a grounding pad.

While the prior art has directed considerable effort towards improving the structure of the body electrode, little attention has been directed towards improving the connector means between the electrode and the conductors which carry the signals or current to the appropriate equipment. Examples of various types of electrical connectors which have been used in the past are shown in prior U.S. Pat. Nos. 3,085,577; 3,581,736; 3,602,216; 3,671,922; 3,750,094 and 3,895,635. None of these prior art electrical connectors have proven to be entirely satisfactory for the intended purpose, however. Obviously, a poor connector can produce totally erroneous signals and distort the readings taken in an EEG or ECG system. More importantly, a loose connector for a grounding pad used in electro-surgery can result in serious burns to the patient. If the grounding pad electrode does not provide a low impedance path for the return current, the current will seek alternative means to return to the electro-surgical unit to complete the circuit. Usually the alternate paths provide high current density and tissue heating and burns on the patient are the likely result. Thus, the provision of a good conducting return path from the grounding pad is essential in order to assure safe, burn free electro-surgery.

According to the present invention there is provided an electrical connector which is adapted to be locked into contact with a headed electrode so that the connector cannot be in advertently removed. When the headed stud of the electrode is locked into position in the connector a conducting path is insured by reason of the fact that conducting fingers are spring urged into contact with the headed stud. The electrical connector is provided with a slidable locking plate having two end positions. In one end position the headed stud of the electrode may be readily inserted or removed from the connector and when the slidable locking bar is moved towards the other end positon a cam surface on the locking bar forces the headed stud into contact with spring-urged contacting tabs in which position the headed stud is firmly locked. The slidable locking bar is provided with a spring-urged pin which engages in a detent or recess in the body of the electrical connector to prevent accidental dislodgement of the slidable locking bar from its locked position.

An object of the present invention is to provide an electrical connector for an electrode wherein means is provided to lock the connector in engagement with the electrode and provide an adequate conducting path from the electrode.

Another object of the present invention is to provide an electrical connector having a slidable locking bar therein with a cam surface which forces the headed stud on an electrode to a locking position when the slidable locking bar is shifted from an open to a locked position.

Figure 5:
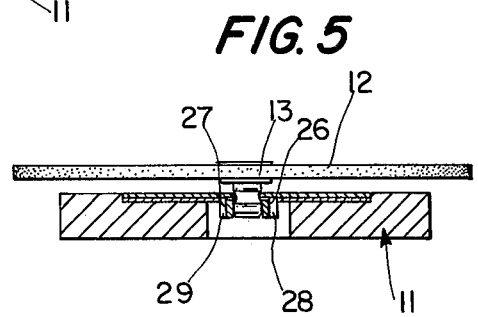
Figure 2:
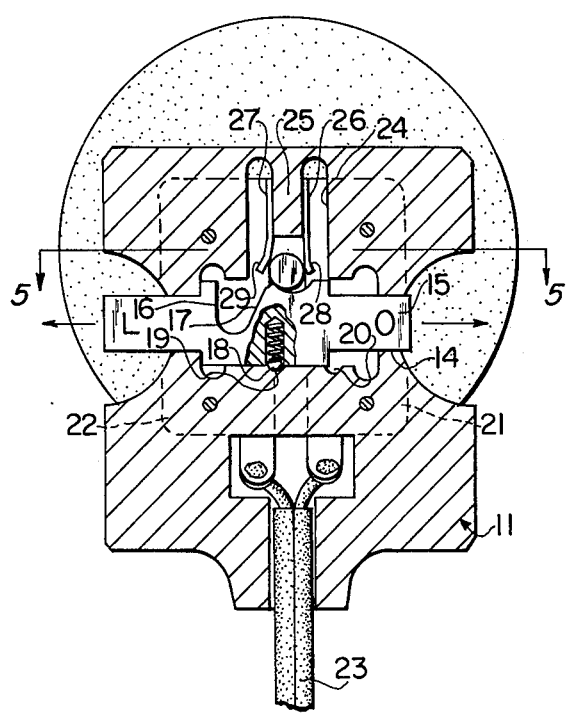
Figure 3:
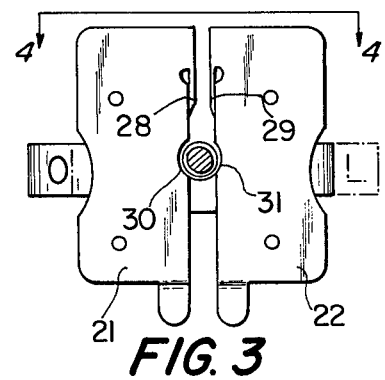
Figure 4:
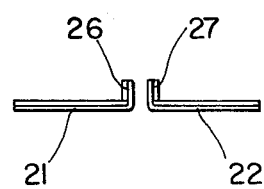

Other objects in many of the intended advantages of the present invention will be come more readily apparent upon consideration of the following detailed specification in connection with the accompanying drawing wherein:

FIG. 1 is a prespective view showing the electrical connector of the present invention attached to an electrode, FIG. 2 is a sectional view through the connector along the line 2—2 of FIG. 1, FIG. 3 is a plan view of the connector showing the electrode stud in both the locked and released positions, FIG. 4 is an end view of contact plates only along the line 4—4 of FIG. 3 and FIG. 5 is a sectional view along the line 5—5 of FIG. 2 showing the headed stud of the electrode in locked position on the connector.

Referring now more specifically to the drawing wherein like numerals indicate like parts throughout the several views there is shown generally at 11 an electrical connector according to the present invention. The connector is adapted to be locked into engagement with an electrode such as an EKG electrode 12 having a headed stud 13 thereon.

The body of the electrical connector 11 may be made of plastic or other suitable insulating material and is provided with a transverse slot 14 which is adapted to receive a slidable locking bar 15. The locking bar 15 has a cut out portion 16 with a cam surface 17 forming a peripheral side of the cut out. Disposed within a bore in the locking bar 15 is a spring-urged ball 18 which is adapted to be received within depressions 19 or 20 to retain the slidable locking bar in the locked or open position respectively.

Secured to one face of the connector lock 11 is a pair on contact plates 21 and 22. Contact plates 21 and 22 are secured to the conductor body 11 so that their adjacent peripheral edges are spaced apart an amount just larger than the diameter of the stud undercut but smaller than the diameter of the stud head as clearly seen in FIG. 3. The plates are electrically connected with conductors 23 which are adapted to carry the signal or current from the electrode 13 to the appropriate electrical equipment.

The connector body 11 is provided with a recess or groove 24 which is disposed normally with respect to the transverse slot 14 which receives the slidable locking bar 15. The recess 24 opens at one end into the slot 14 and at the opposite end of the recess 24 an abutment 25 extends centrally into the recess.

The contact plates 21 and 22 have peripheral edges 26 and 27 respectively which are bent at 90° to the surface of the contact plates to form flanges or tabs as clearly seen in FIG. 4. As seen in FIG. 2 these flanges or tabs 26 and 27 extend into the recess 24 and portions of the tabs 26 and 27 contact the outer surfaces of abutment 25.

The end portions 28 and 29 or tabs 26 and 27 respectively are cut free from the contact plates 21 and 22 so as to form spring contact fingers. The end portions of members 28 and 29 are outwardly bent as seen in FIG. 2 so as to receive the headed stud of the electrode 13 when the electrode is in a locked position.

Referring to FIGS. 2 and 3 it can be seen that centrally of the inner peripheral edges of the contact plates 21 and 22 there is provided concave cut outs 30 and 31 respectively. The concave cut outs 30 and 31 together with the space between the contact plates 21 and 22 forms a circular opening which is sufficiently large to receive the headed stud 13 of the body electrode 12. When the locking bar 15 is in the open position the cut out or recess 16 in the locking bar is disposed directly beneath the circular opening form between concave cut outs 30 and 31. Thus, in this position the headed stud will be received within the cut out in the locking bar 15. As the locking bar is moved to the opposite end position the headed stud 13 is forced by the cam surface 17 on the locking bar into the recess 24 between the spring fingers 28 and 29 of contact plates 21 and 22. In this narrowed portion of the spacing between the contact plates 21 and 22 the headed stud 13 cannot be disengaged from the connector block 11 as clearly seen in FIG. 5. The headed stud is thus retained in position in engagement with the spring contact fingers 28 and 29, the peripheral edges of contact plates 21 and 22 with the stud butting abutment 25 on one side and the locking bar 15 on the opposite side. Thus, the headed stud is retained in a firm locking position in engagement with the spring contact fingers 28 and 29. Thus, an electrical path from the body electrode 12 through the headed stud 13, the spring finges 28 and 29, contact plates 21 and 22 and conductors 23 to the appropriate equipment is assured. This allows a conducting alarm system that insures contact between the electrode stud and the connector. There is no possibility of the headed stud becoming dislodged from the connector as the locking plate must be moved to the open position to permit the headed stud to return to a position between the concave cut outs 30 and 31 in order to be removed from the connector plate.

Obviously many modifications and variations of the present invention are possible in light of the above teachings.

We claim:

1. In combination, an electrode including a stud having an enlarged head thereon, an electrical connector comprising a base plate, a slot in said base plate, a slidable locking element disposed in said slot, a cam surface disposed on said locking element, a recess in said base extending normally with respect to said slot, a pair of electrical contact elements, one of said electrical contact elements being fixed to said base plate on each side of said recess in said base plate whereby edge surfaces of said contact elements are in spaced relation to receive the electrode stud therebetween, an enlarged spacing portion between the contact elements to receive the head of the stud and adjacent thereto a reduced spacing portion between the contact elements of insufficient width to pass the head of the stud therebetween whereby when the electrode and connector are to be attached the headed stud is placed within the recess within the enlarged spacing portion between the contact element and the locking element is moved to bring the cam surface into engagement with the headed stud to force the headed stud to a position within the recess within the reduced spacing portion between the contact elements and to maintain the headed stud in a locked position therein.

2. The combination according to claim 1 and further including portions of said electrical contact elements extending into said recess to engage the surface of said headed stud.

3. The combination according to claim 1 and further including a spring pressed pin in said locking element to retain the locking element in a stud-locking position.

4. The combination according to claim 1 and further including peripheral portions of said electrical contact elements bent into said recess and having end portions thereof forming spring tabs for engagement with the headed stud.

* * * * *